United States Patent [19]

Klemann et al.

[11] Patent Number: 5,045,338
[45] Date of Patent: Sep. 3, 1991

[54] SECONDARY AMIDE ESTERS AS LOW CALORIE FAT MIMETICS

[75] Inventors: Lawrence P. Klemann, Somerville; John W. Finley, Whippany; Ronald G. Yarger, Convent Station, all of N.J.

[73] Assignee: Nabisco Brands, Inc., Parsippany, N.J.

[21] Appl. No.: 409,394

[22] Filed: Sep. 19, 1989

[51] Int. Cl.$^5$ .......................... A23D 7/00; C07H 5/04; C09F 5/00

[52] U.S. Cl. .................... 426/611; 260/404; 260/404.5; 426/531; 426/601; 426/804; 536/18.7; 536/55.2; 536/53

[58] Field of Search ............... 426/601, 611, 531, 804; 260/404, 404.5; 536/18.7, 55.2, 53

[56] References Cited

U.S. PATENT DOCUMENTS

| 519,980 | 5/1984 | Winter . | |
|---|---|---|---|
| 3,495,010 | 2/1970 | Fossel | 424/312 |
| 3,600,186 | 8/1981 | Mattson et al. | 99/1 |
| 3,637,774 | 1/1972 | Babayon et al. | 260/410.6 |
| 3,876,794 | 4/1975 | Rennhard | 426/152 |
| 3,968,169 | 7/1976 | Seiden et al. | 260/615 |
| 4,005,195 | 1/1977 | Jandacek | 257/528 |
| 4,005,196 | 1/1977 | Jandacek et al. | 424/180 |
| 4,046,874 | 9/1977 | Gabby et al. | 424/73 |
| 4,304,768 | 12/1981 | Staub et al. | 424/180 |
| 4,461,782 | 7/1984 | Robbins et al. | 426/549 |
| 4,626,441 | 12/1986 | Wolkstein | 426/548 |
| 4,631,196 | 12/1986 | Zeller | 426/580 |
| 4,678,672 | 7/1987 | Dartey et al. | 426/19 |

FOREIGN PATENT DOCUMENTS 0233856 2/1986 European Pat. Off. .
0236288 2/1986 European Pat. Off. .
0256585 7/1986 European Pat. Off. .
2021579 5/1978 United Kingdom .

OTHER PUBLICATIONS

Chemical Abstracts 65-5513e 1966.
Booth, A. N., 40 JAOCS 551-553 (1963).
Garner, C. W., and Smith, L. C., 39 BBRC 672-682 (1970).
Goodman and Gilman's Pharmacologiacal Basis of Therapeutics, 7th ed, 1002-1003 (1985).
Gottenbos, J. J., Chap. 8 of Dietary Fat Requirements, pp. 107-112 AOCS (1988).
Hamm, D. J., 49 Food Sci. 419-428 (1984).
Haumann, B. J., 63 JAOCS 278-288 (1986).
LaBarge, R. G., 42 Food Tech. 84-90 (1988).
Michael, W. R., and Coots, R. H., 20 Tox. App. Pharm. 334-345 (1971).
Merten, H. L., 18 J. Ag. Food Chem. 1002-1004 (1970).
Inch, T. D., and Fletcher, H. G., J. Org. Chem., 31:1815-1820 (1966).

Primary Examiner—Donald E. Czaja
Assistant Examiner—Evan Federman

[57] ABSTRACT

Secondary amide esters of the general formula

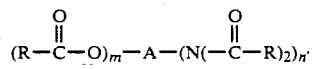

where A is an organic radical having 2 to 6 carbons,
  m = 1 to 3,
  n = 1 to 3, and
each R is, independently, an aliphatic, ether or ester group having 1 or 2 to 29 carbons are edible, preferably partially digestible, fat replacements for foods.

59 Claims, No Drawings

SECONDARY AMIDE ESTERS AS LOW CALORIE FAT MIMETICS

BACKGROUND OF THE INVENTION

This invention relates to the use of secondary amide esters which are acylated aminoalcohol derivatives, notably structures having a two- to six- carbon backbone to which are attached at least one fatty aliphatic, ether or ester $C_1$ or $C_2$ to $C_{29}$ group in ester linkage and at least two other fatty aliphatic, ether or ester groups in secondary amide linkage, as edible, preferably partially digestible, fat replacements in foods and pharmaceuticals.

Reduction in caloric intake can be significantly enhanced by dietary fat reduction, since fats provide nine calories per gram compared to four calories per gram provided by protein or carbohydrates. Furthermore, dietary fats represent approximately 40 to 45% of the U.S. daily caloric intake, and the percentage has risen since 1936 (Merten, H. L., 18 J. Agr. Food Chem. 1002 (1970)). Not only are fats high in calories, but certain fats appear to pose a health risk when consumed in large quantities over time. A number of national advisory committees on nutrition have made recommendations differing in detail, but the common theme is a reduction in the total amount of fat in the diet (Gottenbos, J. J., chapter 8 in Beare-Rogers, J., ed., Dietary Fat Requirements in Health and Development, A.O.C. S. 1988, page 109). Hence, major research efforts have focused on ways to produce food substances that provide the same functional and organoleptic properties as fats, but not the calories.

Mineral oil, sugar fatty acid polyesters, trialkoxytricarballylates, trialkoxycitrates, trialkoxyglyceryl ethers, jojoba wax, silicone oils and various polysaccharides have been suggested for use as edible fat replacements. (For recent reviews, see Hamm, D. J., 49 J. Food Sci. 419 (1984), Haumann, B. J., 63 J. Amer. Oil Chem. Soc. 278 (1986), and La Barge, R. G., 42 Food Tech. 84 (1988).) These low calorie replacement fats, whether they be triglyceride analogues or polymeric materials, are generally engineered to retain fat properties in foods while removing the susceptibility toward hydrolysis during digestion, thus rendering the compounds nonabsorbable or nondigestible.

Side effects from the consumption of nondigestible fat materials have been observed for many years. Mineral oil, patented as an edible fat replacement in a composition as early as 1894 (U.S. Pat. No. 519,980 to Winter), acts as a laxative, interferes with the absorption of water and fat soluble substances, and elicits foreign body reactions in the intestinal mucosa and other tissues (early documented in Stryker, W. A., 31 Arch. Path. 670 (1941), and more recently summarized in Goodman and Gilman's The Pharmacologic Basis of Therapeutics, 7th ed., Macmillan Pub. Co., N.Y., 1985, pp. 1002-1003).

The caloric availability and digestibility of a series of new-type fats, including amylose fatty acid esters, diglyceride esters of succinic, fumaric, and adipic acids, and polymeric fats from stearic, oleic and short-chain dibasic acids, were assessed in the 1960's by the U.S.D.A. at the Southern and Western Regional Research Laboratories (see Booth, A. N., and Gros, A. T., 40 J. Amer. Oil Chem. Soc. 551 (1963) and the references cited therein). Rats fed the experimental fats exhibited undesirable gastrointestinal side effects similar to what had already been observed with mineral oil consumption by people. In several of the balance studies, the diarrhea was so extreme that digestibility coefficients could not be calculated for the trial feedings (ibou., Table I, p. 552).

More recently, sucrose polyesters, nondigestible mixtures of sucrose hexa-, hepta-, and octa- fatty acid esters, have been suggested as low calorie replacements of edible fats and oils in food compositions (U.S. Pat. Nos. 3,600,186 to Mattson and Volpenhein). Sucrose polyesters can also cause undesirable gastrointestinal side effects. In initial trials, the the compounds passed through the body causing frank anal leakage. To combat this, various hardened fats, notably hydrogenated palm oils and synthetic cocoa butters, have been employed as anti-anal leakage agents to be used with the polyesters (U.S. Pat. Nos. 4,005,195 to Jandacek, 4,005,196 to Jandacek and Mattson, and 4,461,782 to Robbins and Rodriguez), and saturated residues have been incorporated into the polyester molecules (Eur. Pat. Ap. Nos. 236,288 to Bernhardt and 256,585 to van der Plank and Rozendaal).

Polyglycerol esters (esterified polymerized glycerol) comprise another class of fat replacements. Linear and cyclic polyglycerols of different chain lengths have been prepared for consumption in food (U.S. Pat. No. 3,968,169 to Seiden and Martin), and substituted with a range of fatty acid residues (U.S. Pat. No. 3,637,774 to Babayan and Lehman) for use in margarine, imitation butter, cheese spreads, dips, puddings, icings, salad dressings, sauces, frozen desserts, including ice cream and sherbet, and the like (U.S. Pat. Nos. 3,637,774, ibid., and 4,046,874 to Gabby et.al.). The fatty acid moieties of this class of fat replacements can be catabolized if the polymer is short, but polyglycerol itself is not metabolized (Michael, W. R., and Coots, R. H., 20 Toxicol. Appl. Pharm. 334 (1971)). And the laxative effect of polyglycerol esters is so pronounced that the compounds have been suggested for use as fecal softeners (U.S. Pat. No. 3,495,010 to Fossel).

Hamm, supra at 427, tested trialkoxytricarballylate, a structural triglyceride analogue with the ester bonds reversed as compared to natural fat, and jojoba wax as possible fat replacements. He found that laboratory rats derived little, if any, caloric value when fed the compounds, but anal leakage of the unabsorbed low calorie oils occurred. At higher dosages, weakness, depression and death were also observed in some animals.

A number of branched and linear polysaccharides have also been suggested as fat replacements in foods. Polydextrose, a tasteless non-sweet low calorie bulking agent formed by th random polymerization of glucose with lesser amounts of sorbitol and citric acid, has been used as a replacement for fat and sugar in a variety of common processed foods, including desserts (U.S. Pat. No. 4,626,441 to Wolkstein), dairy products (U.S. Pat. No. 4,631,196 to Zeller) and crackers (U.S. Pat. No. 4,678,672 to Dartey and Biggs). Polyglucoses and polymaltoses, prepared by the polycondensation of saccharides in the presence of a polycarboxylic acid catalyst, were synthesized and used in dietetic foods in U.S. Pat. No. 3,876,794 to Rennhard. Again, however, it has been found that ingestion of polysaccharides and/or polyols in amounts as low as 30 to 100 grams per day can cause some people to suffer from gastrointestinal discomfort and diarrhea, and dietary fiber preparations have been incorporated into polysaccharide and/or polyol-containing foodstuffs to help inhibit the diarrheal effect (U.S. Pat. No. 4,304,768 to Staub et.al.).

SUMMARY OF THE INVENTION

An object of the present invention is to provide a new group of fat replacement compounds, members of which are more compatible with normal digestion. More particularly, it is an object of a preferred embodiment of the present invention to provide a more digestible fat replacement which interferes less with fat metabolism, thus minimizing or avoiding diarrhea and other laxative side effects. It is a further object of a preferred embodiment of the present invention to provide a partially digestible fat replacement which may, if desired, be engineered to provide essential or desirable fatty acids.

These and other objects are accomplished by the present invention which describes a new class of edible fat mimetics, methods of using them, and food compositions employing them. The compounds of this invention are secondary amide esters, acylated aminoalcohol derivatives which have a two- to six-carbon backbone to which are attached at least one fatty aliphatic, ether, or ester $C_1$ or $C_2$ to $C_{29}$ group in ester linkage and at least two other fatty groups in secondary amide linkage. This new class of edible fat mimetics comprise compounds having the following general

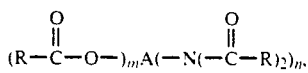

where:

7 15 A is an organic radical having from 2 to 6 carbons, m=1 to 3, n=1 to 3, and each R is, independently, a $C_1$ to $C_{29}$ aliphatic group, a $C_2$ to $C_{29}$ ether group of the formula R'-0-R"-, or a $C_2$ to $C_{29}$ ester group of the formula R"—0—(CO)—R'13 or R'—(CO)—0—R"—, where R'- and R"- are, independently, aliphatic groups.

DETAILED DESCRIPTION OF THE INVENTION

Dioctanoyl-2-amino-1-propanol was synthesized as a lipase substrate for a study of hydrolysis in monomolecular films (Garner, C. W., and Smith, L. C., 39 Biochem. Biophys. Res. Commun. 672 (1970)). Oette and Tschung subsequently suggested aminoglyceride derivatives as phospholipid analogues of possible pharmacological utility in promoting the in vivo formation of natural phospholipids (GB 2,021,579, page 5, line 23). When fed to rats, aminomonoglyceride derivatives were found to be metabolized and accumulated in organ lipids, mostly in the liver, but also in adipose tissue (Oette, K., and Tschung, T. S., 361 Hoppe-Seyler's Z. Physiol. Chem. 1179 (1980)). The authors concluded that these monoglyceride analogues were metabolized to lecithin and cephalin analogues (GB 2,021,579, page 5, line 6).

Garner and Smith's and Oette and Tschung's compounds had fatty acid residues attached to glyceride backbones in one or more primary amide linkages. The present invention is based on the finding that certain acylated aminoalcohols which have a two- to six- carbon backbone which have a secondary amide functionality instead of a primary, i.e., two acyl groups attached to each nitrogen instead of one, exhibit desirable properties when used as edible fat mimetics.

The secondary amide esters of this invention comprise acylated aminoalcohols having the following general formula:

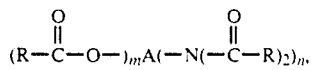

where:

A is an organic radical having from 2 to 6 carbons, m=1 to 3, n=1 to 3, and each R is, independently, a $C_1$ to $C_{29}$ aliphatic group, a $C_2$ to $C_{29}$ ether group of the formula R'-0-R"-, or a $C_2$ to $C_{29}$ ester group of the formula R"—0—(CO)—R'—or R'—(CO)—0—R"—, where R'- and R"- are, independently, aliphatic groups. In general, preferred structures are partially digestible and have m=1 or 2, and n=1 or 2.

The compounds of this invention have a backbone, A, derived from an aminoalcohol, to which are attached at least two aliphatic, ether or ester groups, R, in secondary amide linkage, and at least a third fatty group, R, in ester linkage. The compounds may have as many as 3 secondary amide groups (m) and 3 ester groups (n) attached to backbone A. Thus, this invention comprises acylated aminoalcohols with 3 to 9 fatty substituents, so long as at least two substituents are attached in secondary amide linkage, and at least one is attached in ester linkage. While the minimum number of R groups is always 3 and the maximum can be has high as 9, the preferred compounds of this invention have 3 or 4 R groups (i.e., compounds with one secondary amide functionality and one or two ester functionalities).

Examples of aminoalcohols forming the compound backbones are aminoethanol, aminopropanol, aminopropanediol, diaminopropanol, aminobutanol, diaminobutanol, aminobutanediol, diaminobutanediol, aminopentanol, diaminopentanol, aminopentanediol, diaminopentanediol, aminohexanol, diaminohexanol, aminohexanediol, diaminohexanediol, and the like. Chemical descriptions and formulae used here include isomeric variations.

Instead of being acylic, backbone A may also be derived from a carboxyclic or a heterocyclic of up to 6 carbons. This invention encompasses cyclohexyl derivatives having a six-membered carbon ring (which may be saturated or unsaturated) to which is attached at least one fatty group in ester linkage and at least two fatty groups in secondary amide linkage as described in the general formula supra. Thus, aminocyclohexanols, diaminocyclohexanols, aminocyclohexanediols, diaminocyclohexanediols, their cyclohexene counterparts, and the like, may form the compound backbones.

This invention further encompasses sugar derivatives such as acylated, esterified galactosamine (2-amino-2-deoxygalactose), 2-amino-2-deoxyribose, and the like. In these compounds, the backbone is a heterocyclic having 2 to 6 carbons to which are attached at least one fatty group in ester linkage and at least two in secondary amide linkage as described above.

The R groups have 1 or 2 to 29 carbon atoms, and may be aliphatic groups, ether groups of the formula R'-0-R"—, or ester groups of the formula R"-0-(C0)-R'—or R'-(C0)-0-R"-, where R' and R" are aliphatic groups. The R groups may be the same or different, and may comprise a mixture of fatty groups.

When the R groups are aliphatic, they may be derived from fatty acids of the formula RCOOH. The term "fatty acids" used here means organic fatty acids containing 2 to 30 carbons, and may be synthetic or natural, saturated or unsaturated, with straight or branched chains. Examples of fatty acids that can be used in this invention are acetic, propionic, butyric, caproic, caprylic, pelargonic, capric, undecanoic, lauric, myristic, palmitic, stearic, arachidic, behenic, lignoceric, cerotic, montanic, melissic, palmitoleic, oleic, vaccenic, linoleic, linolenic, eleostearic, arachidonic, nervonic, eicosapentaenoic, docosatetraenoic, docosapentaenoic, and docosahexaenoic acids. Mixtures of fatty acids may also be used, for example, those derived from non-hydrogenated, partially hydrogenated or fully hydrogenated oils such as soybean, safflower, sunflower, sesame, peanut, corn, olive, rice bran, canola, babassu nut, coconut, palm, palm kernel, lupin, nasturtium seed, mustard seed, cottonseed, low erucic rapeseed, butter or marine oils, or obtained from plant waxes such as jojoba. Specific fractions of natural or processed oils may also be used.

When the R groups are ether groups of the formula R'O—R"-, where R' and R" are aliphatic groups as defined above, the ether group (—O—) may occur anywhere in the $C_2$ to $C_{29}$ chain. The chain may be linear or branched, saturated or unsaturated. Ether R derivatives may be derived by using etheric carboxylic acids as acylating agents.

R may also be an ester group of the formula R"—0—(CO)—R'—or R'—(CO)—0—R"—, where R' and R" are as defined above. Thus, R may be a dicarboxylate-extended fatty ester group. By "dicarboxylate-extended" is meant a group formed from the reaction of fatty alcohols of the formula R"OH with dicarboxylic acids such as, for example, malonic, succinic, glutaric or adipic acid. The resulting malonyl-, succinyl-, glutaryl-, or adipoyl- fatty groups are, structurally, aliphatic alcohols with their chains extended by the dicarboxylic acid residue. Thus, malonyl-extended R would have the formula R"—0—(CO)—$CH_2$—, succinyl-extended R would be R"—0—(CO)—$(CH_2)_2$—, glutaryl extended R would be R"—0—(CO)—$(CH_2)_3$—, and so forth.

R may also be an ester group derived from an acylated hydroxycarboxylic acid, and having the ester bond in the opposite direction as compared to dicarboxylate-extended ester groups. Ester R groups of this type are, structurally, either acylated hydroxy fatty acids or fatty acids extended by hydroxycarboxylic acids. Thus, the hydroxyl group of an acid in the lactic acid series, for example, glycolic acid (hydroxyacetic, $CH_2OH$-COOH) or hydracrylic acid (3-hydroxypropionic, $CH_2OH$-$CH_2$-COOH), may be acylated with a fatty acid (R"COOH) to yield an ester R group of the formula R"—(CO)—0—$CH_2$—(glycolic), L R"—(-CO)—0—$(CH_2)_2$—(hydracrylic), and so forth. Any isomer of any hydroxycarboxylic acid may be used with any fatty acid, so long as the sum of the carbons in the hydroxycarboxylic and fatty acid portions of R group is less than or equal to 29. This type of ester R group may also be formed by acylating the hydroxyl group of an hydroxy fatty acid such as ricinoleic acid.

The R groups will be selected to provide a discernible fatty character in the compounds. Thus, many of the R groups have 3 or more carbon atoms, with a percentage containing 3 to 3 carbons (derived from acids having 4 to 24 carbons), more narrowly 9 to 19, and even more narrowly, 15 to 17 carbon atoms (derived from acids having 16 to 18 carbons). However, the R groups attached in secondary amide linkage can be short, i.e., having 1 to 4 carbons (derived from acids having 2 to 5 carbons). Thus, many compounds of this invention have R groups of 1 to 23 carbons. In one embodiment of this invention, for example, all of the R groups attached in secondary amide linkage are short, i.e., having 1 to 4 carbons, while the ester R groups have 13 to 17 carbons. In another embodiment, the R groups attached in secondary amide linkage are mixed, i.e., unequal in length, comprised of a short (1- to 4-carbon) R and a 13- to 17-carbon R. In yet another embodiment, all the R groups have 13 to 17 carbons (derived from fatty acids having 14 to 18 carbons).

The preferred primary amide esters of this invention are partially digestible, and typically provide from about 0.5 to 8.5 kcal/gram, more narrowly 1.0 to 6.0 kcal/gram. In these preferred compounds, the R side groups show differential reactivity toward digestive enzymes, so that the compounds become more hydrophilic when catabolized. The more readily digestible residue R can be an essential or nutritionally desirable fatty acid such as linoleic acid. As with natural triglycerides, the more readily digestible residue R can also be a fatty acid having beneficial attributes, such as, for example, those associated with conjugated linoleic acid isomers.

The secondary amide esters of this invention may be incorporated either alone, or in combination with another fat and/or fat mimetic, into any food composition or used in conjunction with any edible material. The term "edible material" is broad and includes anything edible. Representative of edible materials which can contain the fat mimetic compounds of this invention in full or partial replacement of natural fat are: frozen desserts, e.g., sherbet, ice cream, ices, or milk shakes; puddings and pie fillings; margarine substitutes or blends; flavored bread or biscuit spreads; mayonnaise; salad dressings; filled dairy products such as filled cream or filled milk; dairy or non-dairy cheese spreads; coffee lighteners, liquid and dried; flavored dips; frying fats and oils; reformed and comminuted meats; pet foods; meat substitutes or extenders; whipped toppings; compound coatings; frostings, fillings and icings; cocoa butter replacements or blends; candy, especially fatty candies such as those containing peanut butter or chocolate; chewing gum; breakfast cereals; bakery products, e.g., cakes, breads, rolls, pastries, cookies, biscuits, and savory crackers; mixes or ingredient premixes for any of these; as well as flavor, nutrient, drug or functional additive delivery systems.

The following is a list of representative, but not limiting, examples of secondary amide esters of this invention:

(A) Secondary amide esters having the general formula

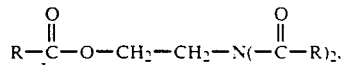

where
each R is, independently, as defined above.
Specific illustrations of this type of secondary amide ester include, for example:
(1) 2-Dioleoylaminoethyl oleate

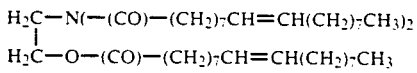

(2) 2-Dimyristoylaminoethyl oleate

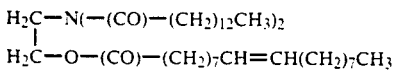

(2) 2-Acetyllauroylaminoethyl palmityl malonate

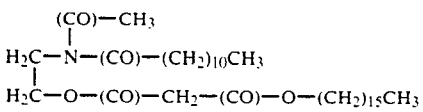

(B) Secondary amide esters which are propyl derivatives having the general formula, $$\begin{array}{l}(CH_2)X\\(CH_d)X_q\\(CH_e)X_t\end{array}$$

where
d = 1 to 2,
e = 2 to 3

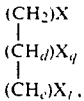
(ester) or $$-N(-\overset{O}{\overset{\|}{C}}-R)_2$$

(secondary amide) groups, subject to the proviso that each molecule contain at least one secondary amide and at least one ester group,
q = 0 to 1,
t = 0 to 1, subject to the proviso that q + t ≧ 1, and R is, independently, as defined above.

Illustrations of this type of secondary amide ester include those having d = e = 2 and q + t = 1 and those having d = 1, e = 2, and q + t = 2 among the following (4) 3-Dioleoylaminopropyl oleate

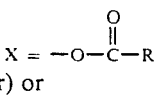

(5) 1-Methyl-2-(dioleoylamino)ethyl oleate

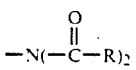

(6) 3-Acetyloleoylaminopropyl 1,2-dioleate

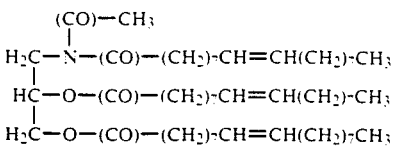

(7) 3-Oxapentanoylstearoylaminopropyl 1,2-dimyristate

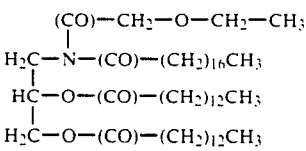

(8) 2-Acetyloloeylaminopropyl 1,3-dioleate

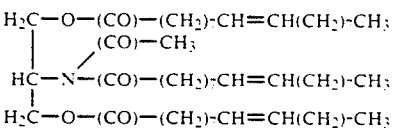

(9) 3-Acetyloleoylaminopropyl palmitate

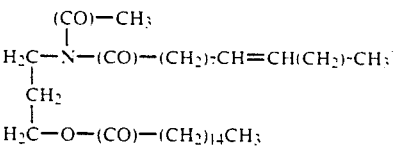

(10) 3-Dioleoylaminopropyl stearate

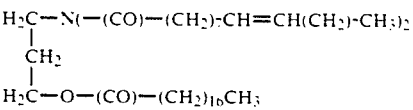

(11) 3-Di(caprylsuccinyl)propyl linoleate

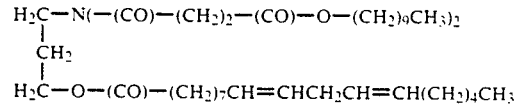

(12) 2-Dioleoylaminopropyl 1,3-dioleate

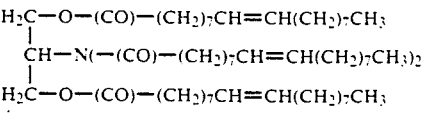

(13) 2-Diacetylaminopropyl 1,3-dioleate

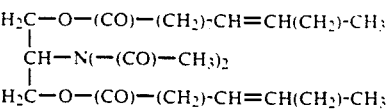

(14) 3-Dioleoylaminopropyl 1,2-dioleate

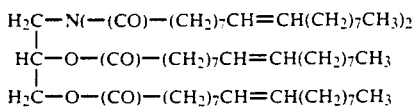

(15) 3-Dimyristoylaminopropyl myristate

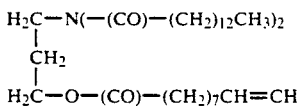

(16) 1,3-Bis-(acetyloleoylamino)propyl 2-opeate

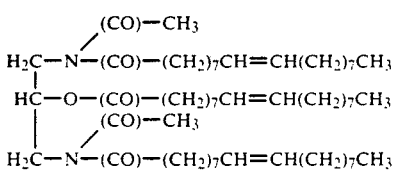

(C) Secondary amide butyl and pentyl esters of this invention which may be described by the general formula, $$\begin{array}{c} (CY_b)X \\ | \\ ((CY_d)X_q)_s \\ | \\ (CY_b)X \end{array}$$

where
b = 1 to 2,
Y = H, —CH$_3$, —CH$_2$CH$_3$, —(CH$_2$)$_2$CH$_3$, or —CH(CH$_3$CH$_3$,
Y being the same or different
d = 1 to 2, subject to the proviso that the numbers of carbons in the backbone is 4 to 5,

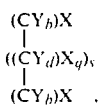
(ester) or

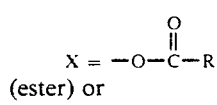

(secondary amide groups, subject to the proviso that each molecule
contain at least one secondary amide and at least one ester group,
q = 0 to 1,
s = 0 to 3, and independent of 1, and each R is, independently, as defined above.

Examples of this type of secondary amide ester include
(17) 3-Acetylmyristoylamino-2-methylpropyl oleate

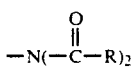

(18) 2-Methyl-3-dioleoylaminopropyl oleate

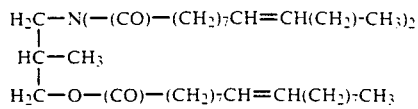

(19) 3-Methyl-3-acetyloleoylaminopropyl 1,2-dioleate

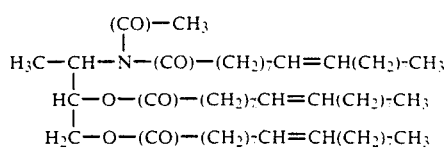

(20) 4-Acetyloleoylaminobutyl 1,2-dioleate

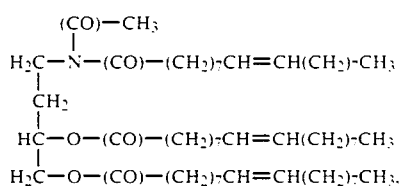

(21) 4-Acetyloleoylaminopentyl 1,3-dioleate

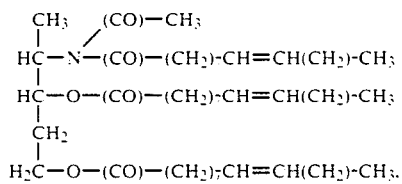

(D) Other secondary amide esters of this invention may be described by the general formula,

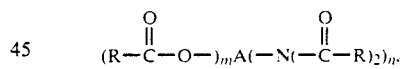

where:
A is an organic radical having 5 to 6 carbons,
m = 1 to 3,
n = 1 to 3, and
each R is, independently, as defined above.

Examples of this type of secondary amide ester derivative include:
(22) 3-Dioleoylaminohexyl 1,4,6-trioleate

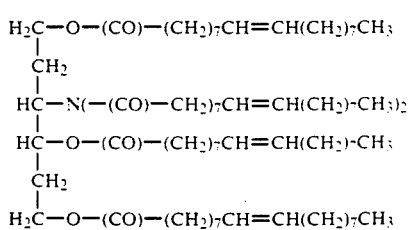

(23) 5-Diacetylaminopentyl 1,3-dipalmitate

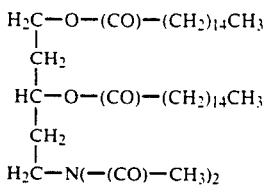

(24) Trans-2-diacetylaminocyclohexyl oleate

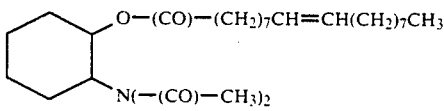

(25) 2-Acetylmyristoylaminocyclohex-4-enyl linoleate

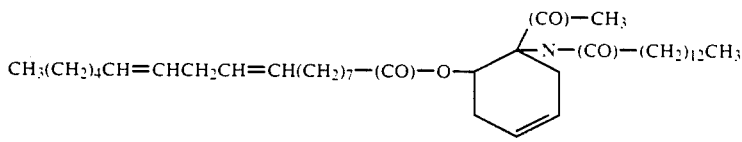

(26) Hexaacylated Galactosamine

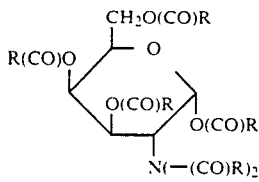

where R is derived from soybean oil
(27) 2-Dilauroylamino-2-deoxyribose trioleate

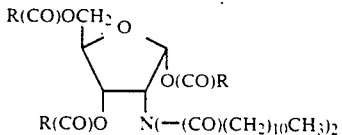

where R = —(CH$_2$)$_6$CH=CH(CH$_2$)$_7$CH$_3$

EXAMPLES

The following examples are presented to further illustrate and explain the present invention and should not be taken as limiting in any regard. Unless otherwise indicated, all parts and percentages are by weight, and are based on the weight at the particular stage of the processing being described. The proton nmr spectra are consistent with the structures for which they are reported.

EXAMPLE 1

3-Dioleoylaminopropyl 1,2-dioleate, a secondary amide ester of this invention, is synthesized in this example.

A solution of 1-amino-2,3-propanediol (9.1 g, 0.1 mole) in 18 mL pyridine is treated with 95 g (0.3 mole) oleoyl chloride with stirring at 0° C. The viscous brown solution is stirred and heated to near reflux for 2 hours, then cooled to room temperature. By-product pyridinium chloride is removed by filtration and the filtrate is diluted with 100 mL ethyl acetate. This solution is washed successively with 5% HCl (2 ×50 mL), water (2×50), and is dried over magnesium sulfate. Filtration and subsequent evaporation affords th title compound as a red-brown oil (85 g). Silica gel chromatography of a 25 g portion of this material (12:1 hexane:ethyl acetate eluant) yields 3.2 g of purified product.

Proton nmr spectrum in chloroform-d: 5.35 and 5.28 (overlapping multiplets, 9 H, HC=CH and methine proton), 4.33 and 3.76 (two doublets of doublets, 2 H, 0—CH$_2$), 4.09 (apparent triplet of doublets, 2 H, N-CH$_2$), 2.80-2.39 (overlapping triptriple lets, 4 H, (—CH$_2$—C0)2N), 2.32 (triplet, 2 H, —CH$_2$—C$_2$—), 2.23 (apparent triplet of doublets, 2 H, —CH$_2$C$_2$—CH), 2.02 (multiplet, 16 H, C=C—CH$_2$—), 1.61 and 1.31 (multiplets, 80 H, —CH$_2$—) and 0.89 (triplet, 12 H, —CHhd 3).

EXAMPLE 2

3-Dioleoylaminopropyl oleate, another secondary

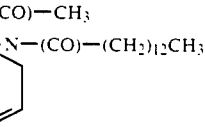

amide ester of this invention, is prepared in this example.

To 7.5 g (0.1 mole) amino-1-propanol in mL pyridine is cautiously added (exothermic reaction!) a solution of 65 g (0.2 mole) oleoyl chloride in 50 mL heptane. After the addition is complete, the mixture is heated to reflux for one hour, then cooled to room temperature and filtered to remove pyridinium chloride. The filtrate is diluted with 100 mL ethyl acetate and is washed successively with 5% HCl (2×50 mL) and water (2×50 mL), and then dried over anhydrous magnesium sulfate. Filtration and subsequent evaporation of the filtrate yields 59 g of a dark red-brown oil. A portion (26 g) of this product is passed through a silica column (12:1 hexane-ethyl acetate eluant) to give 3.8 g of purified oil.

Proton nmr spectrum in chloroform-d: 5.35 (multiplet, 4 H, HC=CH), 4.10 (triplet, 2 H, 0—CH$_2$), 3.72 (triplet, 2 H, NCHCH$_2$), 2.67 (triplet, 4 H, N—(O-C—CH$_2$—)2), 2.30 (triplet, 2 H, —CH$_2$—C$_2$(multiplet, 12 H, C=C—CH$_2$—), 1.89 (multiplet, 2 H, 0—C—CH$_2$—C—N), 1.62 and 1.31 (multiplets, 60 H, —CH$_2$—) and 0.89 (triplet, 9 H, —CH$_3$).

EXAMPLE 3

2-Diacetylaminopropyl 1,3-dioleate, another amide ester of this invention, is prepared in this example.

To a magnetically stirred solution of 1 0 g (1.13 mmole) 2-oleoylamino-1,3-dioleoyloxypropane in 35 mL pyridine at room temperature is added excess acetyl chloride (3 mL, c. 42 mmole) and the yellow-brown solution is heated to reflux for 2 hours. The reaction mixture is then cooled, diluted with 50 mL ethyl acetate, and washed successively with 5% HCl (4× 100 L. 10 mL), saturated aqueous NaCl (1 × 50 mL), and water (1 × 50 mL), and dried over anhydrous magnesium sulfate. Chromatography on silica gel using hexane/ethyl acetate (12/1, v/v) gives 0.2 g of the title compound as an oil.

Proton nmr in chloroform-d: chemical shift in ppm (multiplicity, intensity, assignment): 5.35 (multiplet, 4

H, HC=CH), 4.52–4.34 (two doublets of doublets, 4 H, 0—CH$_2$), 4.23 (multiplet, 1 H, methine proton), 2.38 (singlet, 6 H, acetyl CH$_3$), 2.30 (triplet, 4 H, CH$_2$—CO$_2$), 2.00 (multiplet, 8 H, C=C—CH$_2$), 1.60 (multiplet, 4 H, CH$_2$—C—CO$_2$), 1.30 (multiplet, 40 H, CH$_2$) and 0.88 (triplet, 6 H, CH3).

EXAMPLE 4

2-Acetyloleoylaminopropyl 1,3-dioleate, another secondary amide ester of this invention, is isolated in this example. Approximately 75 mg of this product is obtained by careful chromatography of the above reaction mixture.

Proton nmr in chloroform-d: chemical shift in ppm (multiplicity, intensity, assignment): 5.35 (multiplet, 6 H, HC=CH), 4.50–4.35 (two doublets of doublets, 4 H, 0—CH$_2$), 4.25 (multiplet, 1 H, methine proton), 2.64 (triplet, 2 H, CH$_2$-CON), 2.38 (singlet, 3 H, acetyl CH$_3$), 2.30 (triplet, 4 H, CH$_2$—C0$_2$), 2.02 (multiplet, 12 H, CH$_2$—C=C), 1.60 (multiplet, 6 H, CH$_2$—C—CON), 1.30 (multiplet, 60 H, CH$_2$) and 0.88 (triplet, 9 H, CH$_3$).

EXAMPLE 5

2-Dioleoylaminopropyl 1,3-dioleate, another secondary amide ester of this invention, is synthesized in this example.

To a stirred suspension of 1.97 g (0.0156 mole) serinol hydrochloride in 50 mL pyridine at room temperature is added 18.0 g (0.06 mole) of oleoyl chloride. The brown solution is heated at reflux for one hour, cooled and filtered. The filtrate is washed successively with 5% HCl (3×100 mL), saturated NaCl (50 mL), and water (50 mL) then is dried over magnesium sulfate. Filtration and concentration affords 41.5 g of a dark brown oil. A 20.75 g portion of the product is chromatographed on silica gel using hexane-ethyl acetate-acetic acid (90/10/5; v/v/v) to elute the desired fraction, concentration of which affords 0.8 of the title composition.

Proton nmr spectrum in chloroform-d: chemical shift in ppm (multiplicity, intensity, assignment): 5.35 (multiplet, 8 H, HC=CH), 4.50-4.37 (two doublets of doublets, 4 H, propane CH$_2$—0), 4.25 (quintet, 1 H, methine proton), 2.63 (triplet, 4 H, CH$_2$—CO$_2$), 2.29 (triplet, 4 H, CH$_2$—CON), 2.05 (multiplet, 16 H, C=C=CH$_2$), 1.65 (multiplet, 8 H, 0=C—C—CH$_2$), .30 (multiplet 40 H, CH$_2$) and 0.89 (triplet, 12 H, CH$_2$).

EXAMPLE 6

1-Methyl-2-dioleoylaminoethyl oleate, another secondary amide ester of this invention, is synthesized in this example.

A solution of 7.5 g (0.1 mole) 1-amino-2-propanol in 25 mL pyridine is treated with 60.2 g (0.2 mole) oleoyl chloride at 0° C. The viscous mixture is stirred at room temperature for one hour, diluted with 100 mL ethyl acetate, and washed successively with 5% HCl and water, and then dried over magnesium sulfate. Following filtration, the filtrate is concentrated to give 60.8 g of crude product. A 26.6 g portion of this material is chromatographed over silica gel to give an 8.5 g sample of the title compound.

Proton nmr spectrum in chloroform-d: 5.35 (multiplet, 4 H, HC=CH), 5.09 (multiplet, 1 H, methine proton), 3.96 and 3.62 (two doublets of doublets, 2 H, N—CH$_2$, 2.81-2.59 (overlapping triplets, 4 H, (—CH$_2$—CO)$_2$N), 2.22 (apparent triplet of doublets, 2 H, CH$_2$—C0$_2$), 2.02 (multiplet, 12 H, C=C—CH$_2$), 1.63 and 1.31 (multiplets, 63 H, —CH$_2$—and propyl -CH$_3$) and 0.89 (triplet, 9 H, —CH$_3$).

EXAMPLE 7

3-Acetyloleoylaminopropyl 1,2-dioleamide is prepared in this example.

To a magnetically stirred solution of 9.4 g (0.011 mole) of 2,3-bis(oleoyloxy)propylamine in 15 mL pyridine is added, via syringe, one mL of acetyl chloride. The solution is heated to reflux for 20 minutes whereupon another one mL of acetyl chloride is added. After an additional 60 minutes at reflux, approximately half of the starting material has been converted to product. Continued heating appears to have no affect on conversion. The reaction mixture is filtered, and is washed successively with dilute HCl and water then is dried over anhydrous magnesium sulfate. Chromatography over silica gel (hexane/ethyl acetate, 1:1 by volume) followed by evaporation of the eluate affords 1.45 g of the title compound.

Proton nmr in chloroform-d: chemical shift in ppm (multiplicity, intensity, assignment): 5.35 (multiplet, 6 H, HC=CH), 5.28 (multiplet, 1 H, methine proton), 4.32, 4.11, 4.08 and 3.75 (four doublets of doublets, each 1 H, CH$_2$—N and CH$_2$—0), 2.70 (multiplet, 2 H, CH$_2$—CON), 2.41 (singlet, 3 H, CH$_3$—CON), 2.30 (three triplets, 4 H, CH$_2$—CO$_2$), 2.02 (multiplet, 12 H, CH$_2$—C=C), 1.60 (multiplet, 6 H, CH$_2$—C—CO), 1.30 (multiplet, 30 H, CH$_2$) and 0.89 (triplet, 9 H, CH$_3$).

EXAMPLE 8

3-Dimyrystoylaminopropyl myristate, another secondary v amide ester of this invention, is prepared in this example.

To 7.5 g (0.1 mole) 3-amino-1-propanol is cautiously added a solution of 50 g (0.2 mole) myrsitoyl chloride in a flask equipped with a magnetic stirrer bar and a vacuum adapter. After the addition is complete, the mixture is heated under vacuum for one hour, then cooled slightly and filtered through silica prior to cooling to room temperature to obtain the product as a solid.

EXAMPLE 9

This example outlines the procedure for estimating the in vitro digestibility of the synthetic fat mimetics of this invention.

Preparation of Reagents and Materials

1. Buffer: A pH 7.1 phosphate buffer is prepared by dissolving 6.8 g KH$_2$PO$_4$ in 1 L of millipore filtered water (to yield 0.05 M phosphate). Fifty mg Ca(NO$_3$)$_2$ is added and 5.0 g. cholic acid (Na salt, an ox bile isolate from Sigma) to give 0.3 mM Ca++ and 0.5 % cholic acid in 0.05 M phosphate. The pH is adjusted to approximately 7.1 with solid NaOH. Several drops of Baker "Resi-analyzed" toluene are added to prevent bacterial growth during storage at 3°-5° C. 2. Lipase: About 15 mg/mL commercial porcine pancreatic lipase from U.S. Biochemical Corporation is dissolved in buffer. 3. Substrates and Standards: A 1.0 mL volumetric flask is charged with an amount of lipid substrate calculated to give a concentration of 200 nanomoles per microliter in Baker "Resianalyzed" toluene. (The proper concentration may be approximated by doubling the molecular weight of the lipid in question, dividing by 10, and diluting to the mark; this yields about 200 nanomoles per microliter.) This preparation affords the substrate to be used in the hydrolysis reactions.

Fatty acids and glyceride standards from Nu Chek or Sigma are prepared for elution on thin layer chromatography (TLC) plates (prewashed with 1:1 chloroform/methanol) by diluting the substrate solution with 10:1 toluene (1 part substrate plus 9 parts toluene by volume) in septum vials.

Procedure

In a 25 mL Erlenmeyer, emulsify 20 mL buffer and 40 microliters of substrate using an ultrasonic disrupter at a microtip maximum setting for approximately 10 seconds. This results in a 0.4 microliter/milliliter emulsion. Place in a 37° C. water bath and stir vigorously. After temperature equilibration, add 40 microliters of enzyme solution and start timing. Remove 5.0 mL aliquots at convenient time intervals for analysis. To establish a standard curve for triolein, aliquots are taken at 10, 20, 30 and 40 minutes. A zero time control should be run for all test compounds.

Add the aliquot to a 15 mL glass centrifuge tube containing a drop of concentrated HCl. Add approximately 3 mL of a 2:1 mixture of $CHCl_3:CH_3OH$ (by volume) and shake vigorously. Centrifuge at approximately 5000 rpm for 5 minutes and transfer the bottom layer with a Pasteur pipet to a 5 mL septum vial. Repeat the extraction step once and combine the two bottom layers. Evaporate the solvent in nitrogen gas. After about half of the solvent is removed, add an equivalent volume absolute ethanol and continue evaporation in a nitrogen stream until dryness is achieved. Samples may be warmed with a heat gun to facilitate drying.

When the samples are dry, add exactly 200 microliters of toluene containing 10% DMSO, cap tightly, and spot TLC plate with 2.0 microliters per channel. (If 100% extraction efficiency of a zero time control is achieved, this amounts to 20 nanomoles of substrate spotted on the plate.) Develop with a suitable solvent system, for example, hexane: ethyl ether: chloroform: acetic acid in a volume ratio of 60:20:20:1. After 15 cm elution, dry plate with a heat gun and determine amounts of starting substrate and products of hydrolysis by scanning 10 to 20 nanomoles per channel at a wavelength of 190 nm using a CAMAG TLC Scanner II densitometer equipped with a Spectra Physics 4270 integrator and comparing with controls run at the same time.

Results

Using this procedure and enzyme system, triolein, a triglyceride control, is substantially hydrolyzed in 10 minutes. Under the same conditions, 2-acetyloleoylaminopropyl 1,3-dioleate, a secondary amide ester synthesized in Example 4, is not hydrolyzed in three hours. Similarly, 2-dioleoylaminopropyl 1,3-dioleate, a secondary amide ester synthesized in Example 5, is not hydrolyzed in three hours.

Example 10

Sweet Chocolate. A low calorie sweet chocolate may be prepared by combining:

| Ingredient | parts |
| --- | --- |
| Cocoa Powder | 1.0 |
| Sugar | 1.0 |
| To this is added a portion of | |
| Example 8 Secondary Amide Ester | 1.0 | and the ingredients are mixed thoroughly and passed through a refiner to reduce the particles to desired size. The material is conched, and the remaining secondary amide ester is added. The mixture is poured into molds and quench cooled. No tempering regimen is necessary.

Chocolate Chips. The chocolate prepared above may be melted and deposited into nibs in the usual process.

EXAMPLE 11

Sugar Cookies. Sugar cookies may be prepared by blending:

| Ingredient | parts |
| --- | --- |
| Sugar | 231 |
| Example 1 Secondary Amide Ester | 114 |
| Salt | 3.7 |
| Sodium Bicarbonate | 4.4 |
| Water | 37.4 |
| 5.9% Dextrose Solution (wt/wt) | 58.7 |
| Flour | 391 |

All of the ingredients are creamed together. The dough so formed may be extruded and baked by the usual process.

EXAMPLE 12

Margarine. Margarine may be prepared by combining the ingredients for the following two phases:

| | parts |
| --- | --- |
| Oil Phase Ingredients | |
| Example 7 Secondary Amide Ester | 59.0 |
| Soybean Hardstock (IV 65) | 40.0 |
| Emulsifier | 1.0 |
| Aqueous Phase Ingredients | |
| Water | 95.8 |
| Milk Solids | 2.0 |
| Salt | 2.0 |
| Citric Acid | 0.1 |
| Beta Carotene | 0.1 |

The phase are emulsified in an oil:aqueous phase ratio of 80:20, and passed through a cool scraped surface heat exchanger in the usual process.

EXAMPLE 13

Flavor Bits. Flavor bits for incorporation into baked goods may be prepared by combining the following ingredients:

| Ingredient | parts |
| --- | --- |
| Sucrose | 215 |
| Water | 180 |
| Corn Syrup | 160 |
| Example 12 Margarine | 28 |
| Flavor | 12 |
| Citric Acid | 10 |
| Glycerine | 8 |
| Salt | 5 |
| Dye | 1 |

The first three ingredients are heated to 290° F. and the heat removed. Margarine is mixed in, and the mixture allowed to cool to 160°-170° F. before adding the remaining ingredients. (Almost any flavoring material may be used as flavor, for example, butterscotch or nut.) The mixture is then poured into a cold aluminum pan and frozen in dry ice. The frozen mixture is then cracked and milled into bits.

EXAMPLE 14

Butterscotch Cookies. Butterscotch cookies may be prepared by blending:

| Ingredient | parts |
| --- | --- |
| Flour | 22.0 |
| Example 2 Secondary Amide Ester | 20.0 |
| Salt | 0.7 |
| Sodium Bicarbonate | 0.1 |
| Monocalcium Phosphate | 0.1 |
| Vanillin | 0.1 |
| Water | 8.0 |
| and mixing well. To this is added | |
| Sugar | 30.0 |
| which is mixed until dispersed. Then add | |
| Example 13 Butterscotch Bits | 19.0 | and mix until just blended prior to depositing and baking by the usual process.

EXAMPLE 15

Vanilla Wafers. Combine and mix well:

| Ingredient | parts |
| --- | --- |
| Flour | 40 |
| Sugar (10X) | 28 |
| Example 6 Amide Ester | 13 |
| Frozen Whole Eggs | 6.0 |
| High Fructose Corn Syrup | 4.0 |
| Salt | 0.7 |
| Vanilla | 0.3 |
| Sodium Bicarbonate | 0.3 |
| Sodium Aluminum Phosphate | 0.1 |
| Ammonium Bicarbonate | 0.1 |
| Water | 7.5 |

Aerate, deposit onto a baking surface and bake in the usual manner.

EXAMPLE 16

Chocolate Chip Cookies. Chocolate chip cookies may be prepared using the butterscotch cookie recipe of Example 14, but substituting

| Ingredient | parts |
| --- | --- |
| Example 12 Margarine | 10.0 |
| Example 4 Secondary Amide Ester | 10.0 |
| for the fat mimetic ingredient, | |
| Granulated Sugar | 15.0 |
| Brown Sugar | 15.0 |
| for the sugar, and | |
| Example 10 Chocolate Chips | 19.0 |
| for the butterscotch bits. | |

EXAMPLE 17

Filled Cream. To make a "filled cream" composition, homogenize about

| Ingredient | parts |
| --- | --- |
| Example 7 Secondary Amide Ester | 30 |
| Skim Milk | 69.9 |
| Polysorbate 80 | 0.1 |
| in a conventional dairy homogenizer. | |

EXAMPLE 18

Ice Cream. Vanilla ice cream may be prepared by mixing

| Ingredient | parts |
| --- | --- |
| Sugar (10X) | 15.0 |
| Nonfat Dry Milk | 3.9 |
| Salt | 0.4 |
| into Water | 39.0 |
| for 3 minutes. Then add melted | |
| Example 8 Secondary Amide Ester | 28.4 | and cook to 200° F. while mixing. Hold for 1 mixture. Cool to 160° F., and add

| Sugared Egg Yolks | 12.5 |
| --- | --- |
| Vanilla Extract | 0.8 | and mix 1 mixture. Cool and freeze to desired overrun.

EXAMPLE 19

Filled Milk. To prepare a "filled milk" composition, combine about

| Ingredient | parts |
| --- | --- |
| Example 17 Filled Cream | 100 |
| Skim Milk | 900 |
| and rehomogenize. | |

EXAMPLE 20

Cheese Products. To prepare cheese products, treat

| Ingredient | |
| --- | --- |
| Example 19 Filled Milk | . | made with a 1:1 mixture of Examples 1 and 8 secondary amide esters is used like natural milk in the normal cheese making process (as is practiced, for example in the production of Cheddar or Swiss cheese). Preferably add

| | parts |
| --- | --- |
| Butter Oil | 10 | to the fat mimetic portion of the filled milk product before it is employed in this process to enhance the proper flavor development of the cheese products.

EXAMPLE 21

Butter Cream Icing. Butter cream icing may be prepared by blending:

| Ingredient | parts |
| --- | --- |
| Sugar | 227.0 |
| Example 3 Secondary Amide Ester | 70.8 |
| Water | 28.4 |
| Nonfat Dry Milk | 14.0 |
| Emulsifier | 1.4 |
| Salt | 1.0 |
| Vanilla | 1.0 |

All of the ingredients are creamed in a mixer at medium speed.

EXAMPLE 22

Crackers. A dough prepared by mixing together.

| Ingredient | parts |
|---|---|
| Flour | 100 |
| Sugar | 5.0 |
| Malt | 1.5 |
| Example 4 Secondary Amide Ester | 7.5 |
| Salt | 1.0 |
| Sodium Bicarbonate | 0.9 |
| Nonfat Dry Milk | 2.5 |
| High Fructose Corn Syrup | 2.5 |
| Monocalcium Phosphate | 0.75 |
| Water | 28 | is sheeted, stamped, and baked to produce a cracker product.

EXAMPLE 23

Sprayed Crackers. The sheeted and stamped cracker dough of Example 22 may be sprayed with the secondary amide ester of Example 1 after baking.

EXAMPLE 24

| Ingredient | parts |
|---|---|
| Water | 5.0 |
| to Sugar | 1.5 |
| and Spices | 3.5 | and mixing three mixtures. To this is added

| Salted Egg Yolks | 8.0 |
|---|---|
| followed by mixing two minutes, and adding | |
| Example 1 Secondary Amide Ester | 40 |
| Corn Oil | 40 |
| then 120 Distilled Vinegar | 2.0 |

The mixture is blended 3 minutes and passed through a colloid mill set at 60 prior to filling in the usual process.

EXAMPLE 25

Pudding. Pudding can be prepared from the following formulation:

| Ingredient | parts |
|---|---|
| Milk | 67 |
| Sugar | 11 |
| Starch | 5 |
| Water | 9 |
| Flavor | 3 |
| Example 1 Secondary Amide Ester | 5 |

The ingredients can be blended together and heated to form a pudding.

EXAMPLE 26

Frying Oil. The secondary amide of Example 6 with 1 ppm polydimethylsiloxane may be used for frying food snacks. For frying potatoes, omit the polydimethylsiloxane.

EXAMPLE 27

Frying Oil. Another frying oil may be prepared to blending one part frying oil of Example 26 with one part peanut oil.

EXAMPLE 28

Pet Food. Dry, expanded animal food kibs may be prepared from the following ingredients:

| Ingredient | parts |
|---|---|
| Hominy Feed | 37 |
| 52% Meat Meal | 17 |
| Wheat Shorts | 13 |
| Example 6 Secondary Amide Ester | 16 |
| Corn Germ Meal | 9.6 |
| Wheat Germ Meal | 3 |
| Dried Milk | 0.9 |
| Beet Pulp | 1.7 |
| Fish Scrap | 0.5 |
| Brewer's Yeast | 0.5 |
| Salt | 0.5 |
| Vitamins and Minerals | 0.1 |

The ingredients are mixed together and water added to raise the water content to 27%, before extrusion, pelleting, and drying in the usual manner.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

What is claimed is:

1. A fat mimetic compound of the following formula, useful as fat replacement in edible materials:

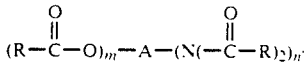

where:
A is an aliphatic group having from 2 to 6 carbons,
m = 1 to 3,
n = 1 to 3, and
each R is, independently, a $C_1$ to $C_{29}$ aliphatic group, a $C_2$ to $C_{29}$ ether group of the formula R'—O—RA—, or a $C_2$ to $C_{29}$ ester group of the formula R"—O—(CO)—R'— or R'—(CO)—O—R"—,
where R'— and R"— are, independentaly, aliphatic groups.

2. The compound according to claim 1 wherein A contains 3 carbon atoms.

3. The compound according to claim 1 wherein m = 1 and n = 1.

4. The compound according to claim 1 wherein m = 2 and n = 1.

5. A fat mimetic compound of the following formula, useful as fat replacement in edible materials:

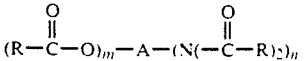

wherein

A is selected from the group consisting of cyclohexyl and aminosugar derivatives having up to 6 carbons,
m = 1 to 3,
n = 1 to 3, and
each R is, independently, a $C_3$ to $C_{29}$ aliphatic group, A $C_2$ and $C_{29}$ ether group of the formula R'—O—R"—,
or a $C_2$ to $C_{29}$ ester group of the formula R"—O—(CO)—R'— or R'—(CO)—O—R",
where R'—and R"—are, independently, aliphatic groups.

6. The compound according to claim 1 wherein the R groups are aliphatic groups.

7. The compound according to claim 6 wherein one R group has 1 to 4 carbons.

8. An edible acylated aminoethanol compound of the formula,

R—(CO)—O—CHJ$_2$—CH$_2$—N(—(CO)—R)$_2$' where each R is, independently, an aliphatic, ether ester group having 1 to 29 carbons.

9. A secondary amide ester compound of the following formula, useful s a fat replacement in edible materials:

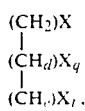

where
d = 1 to 2,
e = 2 to 3,
X = O—(CO)—R (ester) or —N(—(CO)—R)$_2$. (secondary amide) groups, subject to the proviso that each molecule contain at least one secondary amide and at least one ester group
q = 0 to 1,
t = 0 to 1,
subject to proviso that q+t ≥ 1, and
each R is, independently, a $C_1$ to $C_{29}$ aliphatic group, a $C_2$ to $C_{29}$ ether group of the formula R'—O—R"—,
or a $C_2$ to $C_{29}$ ester group of the formula R"—O—(CO)—R'— or R'—(CO)—O—R"—,
where R'—, and R"— are, independently, aliphatic groups.

10. The compound according to claim 9 wherein d = e = 2 and q+t = 1.

11. The compound according to claim 9 wherein d = 1, e = 2, and q+t = 2.

12. A compound of the following formula, useful as a fat replacement in edible materials:

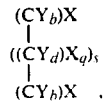

where
Y = H, —CH$_3$, —CH$_2$CH$_3$, —(CH$_2$)$_2$CH$_3$, or —CH(CH$_3$)CH$_3$,
each Y being the same or different, subject to the proviso that the number of carbons in the backbone be 4 to 5, b = 1 to 2,
d = 1 to 2,

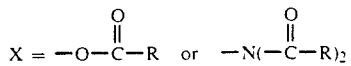

groups, subject to the proviso that each molecule contain at least one secondary amide and at least one ester group,
q = 0 to 1,
s = 0 to 3, independent of q,
and each R is, independently, a $C_1$ to $C_{29}$ aliphatic group,
a $C_2$ to $C_{29}$ ether group of the formula R'—O—R"—,
or a $C_2$ to $C_{29}$ ester group of the formula R"—O—(CO)—R'— or R'—(CO)—O—R"—, where R', and R" are, independently, aliphatic groups.

13. The compound according to claim 12 wherein s = 1 = q = 1.

14. The compound according to claims 1 to 13 wherein the R groups are aliphatic.

15. The compound according to claim 14 wherein one R group has 1 to 4 carbon atoms.

16. The compound according to claim 14 wherein two R groups have 3 to 23 carbon atoms.

17. The compound according to claims 1 to 13 wherein said R groups are ether or ester groups.

18. The compound according to claims 1 to wherein said R groups are derived from fatty acids selected from the group consisting of acetic, propionic, butyric, caproic, caprylic, pelargonic, capric, undecanoic, lauric, myristic, palmitic, stearic, arachidic, behenic, lignoceric, cerotic, montanic, melissic, palmitoleic, oleic, vaccenic, linoleic, linolenic, eleostearic, arachidonic, nervonic, eicosapentaenoic, docosatetraenoic, docosapentaenoic, and docosahexaenoic acids, and mixtures thereof.

19. The compound according to claim 1 to 13 wherein said R groups are derived from nonyhdrogenated, partially hydrogenated or fully hydrogenated oils selected from the group consisting of soybeam, safflower, sunflower, sesame, peanut, corn, olive, rice bran, canola, babassu nut, coconut, palm, palm kernel, lupin, nasturtium seed, mustard seed, cottonseed, or erucic rapeseed, butter, marine oils, and fractions thereof.

20. A fat-containing food composition comprising in addition to other ingredients, an acylated aminoalcohol having a two-to six-carbon backbone to which are attached at least two fatty acid residues in secondary amide linkage and at least one fatty acid residue in ester linkage.

21. The composition according to claim 20 wherein the amino-alcohol is selected from the group consisting of aminoethanol, aminopropanol, aminopropanediol, diaminopropanol, aminobutanol, diaminobutanol, aminobutanediol, aminopentanol, aminopentanedio, diaminopentanol, aminocyclohexanol, diaminocyclohexanol, aminocychlohexanediol, galactosamine, and aminodeoxyribose.

22. The composition according to claim 20 wherein said aminoalcohol is a propyl derivative and said number of fatty acid residues is 3.

23. The composition according to claim 20 wherein the fatty acid residues comprise those derived from $C_2$ to $C_{30}$ fatty acids.

24. The composition according to claim 23 wherein two of the fatty acid residues comprise those derived from $C_{14}$ to $C_{18}$ fatty acids.

25. The composition according to claim 23 wherein one fatty acid residue attached in secondary amide linkage is derived from a $C_2$ to $C_5$ fatty acid, and the remaining fatty acid residues are derived from $C_{14}$ to $C_{18}$ fatty acids.

26. The composition according to claim 23 wherein all the fatty acid residues attached in secondary amide linkage are derived from $C_2$ to $C_5$ fatty acids, and the remaining fatty acid residues are derived from $C_{14}$ to $C_{18}$ fatty acids.

27. A method for reducing the available calories in a food composition having an edible oil component, which method consists of replacing at least a substantial portion of the edible oil with a compound of the formula

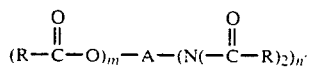

where:
A comprises a 2- to 5- carbon backbone,
m = 1 to 3,
n = 1 to 3, and
each R is, independently, a $C_1$ to $C_{29}$ aliphatic group, A $C_2$ to $C_{29}$ ether group of the formula R'—O—R'—, or a $C_2$ to $C_{29}$ ester group of the formula R'—O—(-CO)—R'— or R'—(CO)—O—R"—,
where R'— and R"— are, independently, aliphatic groups.

28. The method of claim 27 wherein the R groups are selected to produce a discernible fatty character in the compounds.

29. The method of claim 27 wherein m = 1, n = 1, and the R groups are aliphatic groups.

30. A food composition comprising, in addition to other ingredients, an edible fat ingredient of the formula

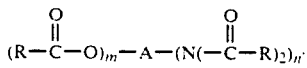

where:
A comprises a
2- to 6- carbon backbone,
m = 1 to 3,
n = 1 to 3, and
each R is, independently, a $C_1$ to $C_{29}$ aliphatic group, a $C_2$ to $C_{29}$ ether group of the formula R'—O—R"—, or a $C_2$ to $C_{29}$ ester group of the formula R"—O—(-CO)—R'— or R'—(CO)—O—R"—,
where R'— and R"— are, independently, aliphatic groups.

31. The composition of claim 30 wherein said food composition is a cookie.

32. The composition of claim 31 further comprising sugar, salt, sodium bicarbonate, water, dextrose solution, and flour.

33. The composition of claim 31 further comprising flour, salt, sodium bicarbonate, monocalcium phosphate, vanilla, water and sugar.

34. The composition of claim 33 further comprising butterscotch bits.

35. The composition of claim 33 comprising chocolate chips, margarine, and brown sugar.

36. The composition of claim 30, wherein said food composition comprises a cracker.

37. The composition of claim 36, wherein said cracker further comprises flour, sugar, malt, sodium bicarbonate, nonfat dry milk, high fructose corn syrup, monocalcium phosphate, and water.

38. The composition of claim 30 wherein said food composition comprises a dairy product.

39. The composition of claim 38 said dairy product is selected from the group consisting of filled milk, filled cream, ice cream, and cheese.

40. The composition of claim 39 herein said filled milk and filled cream further comprise skim milk.

41. The composition of claim 39 wherein said ice cream further comprises skim milk, sugar, gelatin, flavor, and color.

42. The composition of claim 30 wherein said food composition comprises a frying oil.

43. The composition of claim 42 further comprising peanut oil.

44. The composition of claim 30 wherein said food composition comprises margarine.

45. The composition of claim 44 wherein said margarine further comprises soybean hardstock, emulsifier, water, milk solids, salt, citric acid, and beta carotene.

46. The composition of claim 30 wherein said food composition comprises pudding.

47. The composition of claim 47 further comprising milk, sugar, starch, water and flavor.

48. The composition of claim 30 wherein said food composition comprises a pet food.

49. The composition of claim 48 further comprising hominy feed, meat meal, wheat shorts, corn germ meal, wheat germ meal, dried milk, beet pulp, fish scrap, brewer's yeast, salt, vitamins and minerals.

50. The composition of claim 30 wherein said food composition comprises mayonnaise.

51. The composition of claim 50 further comprising corn oil, salted egg yolks, sugar, spices, vinegar, and water.

52. The composition of claim 30 wherein said food composition comprises butter cream icing.

53. The composition of claim 52 further comprising sugar, water, nonfat dry milk, emulsifier, salt and vanilla.

54. The composition of claim 30 wherein the R groups are aliphatic groups having 1 to 23 carbons.

55. In a food composition containing a digestible fat ingredient, the improvement wherein at least a portion of the digestible fat ingredient is replaced by a fat composition characterized by the presence of a $C_2$ to $C_{30}$ fatty acid ester and a $C_2$ to $C_{30}$ fatty acid secondary amide attached to a two- to six-carbon backbone.

56. The improvement of claim 55 wherein the fatty acid ester and fatty acid secondary amide are derived from fatty acids having 2 to 24 carbon atoms.

57. The improvement of claim 56 wherein the backbone has three carbons.

58. The improvement of claim 55 wherein the fat composition is partially digestible.

59. The improvement of claim 55 wherein the fat composition delivers 0.5 to 8.5 kcal/gram.

* * * * *